United States Patent
Loescher et al.

(10) Patent No.: US 6,209,539 B1
(45) Date of Patent: Apr. 3, 2001

(54) ASYMMETRIC PATIENT ADAPTER FOR VENTILATOR CIRCUITS

(75) Inventors: Thomas C. Loescher, Rancho Santa Fe; Dennis Fitzwater, Murrieta, both of CA (US)

(73) Assignee: Hudson Respiratory Care Inc., Temscula, CA (US)

( * ) Notice: Subject to any disclaimer, the term of this patent is extended or adjusted under 35 U.S.C. 154(b) by 0 days.

(21) Appl. No.: 09/273,702

(22) Filed: Mar. 22, 1999

(51) Int. Cl.⁷ .................................................. A61M 16/00
(52) U.S. Cl. ................... 128/204.18; 128/204.17
(58) Field of Search ..................... 128/911, 912, 128/207.16, 207.14, 200.26, 207.15, DIG. 26, 204.16–204.18, 207.18; 604/171, 159, 160, 163

(56) References Cited

U.S. PATENT DOCUMENTS

| | | |
|---|---|---|
| 3,856,051 | 12/1974 | Bain . |
| 4,244,363 | 1/1981 | Moore, Jr. et al. ............. 128/205.17 |
| 4,265,235 | 5/1981 | Fukunaga . |
| 4,281,652 | 8/1981 | Miller . |
| 4,385,629 * | 5/1983 | Wolf, Jr. et al. ................ 128/207.14 |
| 4,838,258 * | 6/1989 | Dryden et al. .................. 128/204.18 |
| 5,228,436 * | 7/1993 | Parkin ............................. 128/205.12 |
| 5,309,906 * | 5/1994 | LaBombard .................... 128/207.14 |
| 5,368,017 * | 11/1994 | Sorenson et al. ............... 128/200.26 |
| 5,404,873 | 4/1995 | Leagre et al. . |
| 5,640,951 * | 6/1997 | Huddart et al. ................. 128/204.77 |
| 5,701,887 * | 12/1997 | Rustad et al. ................... 128/204.17 |
| 5,823,184 * | 10/1998 | Gross .............................. 128/204.18 |
| 5,988,164 * | 11/1999 | Paluch ............................ 128/203.26 |

FOREIGN PATENT DOCUMENTS 298 23 091 U1 4/1999 (DE) .

OTHER PUBLICATIONS

Hudson RCI Catalog, pp. 6,7,8,9,24 and 25, Mar., 1998.

\* cited by examiner

*Primary Examiner*—Dennis Ruhl
*Assistant Examiner*—Teena Mitchell
(74) *Attorney, Agent, or Firm*—Knobbe, Matens, Olson & Bear, LLP

(57) ABSTRACT

A patient adapter for being connected to gas tubing in a ventilator circuit comprises of an inspiratory and an expiratory pipe, the latter having an internal diameter at least about 20% greater than the diameter of the inspiratory pipe. The invention also includes a respirator circuit in which an expiratory limb has an internal diameter at least about 20% greater than the diameter than the inspiratory tubing limb.

16 Claims, 2 Drawing Sheets

ASYMMETRIC PATIENT ADAPTER FOR VENTILATOR CIRCUITS

BACKGROUND OF THE INVENTION

High frequency ventilation (HFV) is widely used in ventilation of premature infants because it operates at substantially lower intrapulmonary pressures as compared to conventional positive-pressure ventilation. HFV administers breathing cycles at above about 120 breaths per minute (2 Hz) and as high 1320 breaths per minute (22 Hz) at very low tidal volumes of between about 5 and about 30 ml. Such low volume and high ventilatory rates dictate the use of ventilator circuits having relatively low energy loss and low internal compliance as compared to circuits used with conventional ventilators and ventilation techniques. At the present, ventilator circuits used in administering high frequency ventilation incorporate inspiratory and expiratory tubing limbs of equal tubing diameter, commonly 10 mm inner diameter (ID). The high frequency ventilator circuits include a patient adapter which is substantially symmetrical, having two small diameter pipes each having an outer diameter (OD) of about 10 mm for connecting the tubing. The pipes intersect with a larger diameter pipe for being connected to an endotracheal or tracheotomy tube. Examples of such circuits are neonatal ventilator circuits manufactured and marketed by Hudson Respiratory Care Inc and HFV circuits manufactured and marketed by Purtian Bennett.

In the administration of high frequency ventilation, flow dynamics of inspiratory and expiratory gas flows are particularly critical because of the manner in which the gas is injected into the patient airways at very high flow rates for very brief time intervals. Typically, gas in HFV is delivered at flow rates of up to 50 liters per minute, but because the pressure is administered for only a fraction of a second, only a small amount of gas actually arrives at the distal airways. Moreover, the patient exhales at the same time and against the flow of gas, quite unlike conventional ventilation in which the inspiratory and expiratory cycles occur independently and the inspiratory gas flow is terminated as expiration begins. Accordingly, for HFV, it is desirable to minimize the expiratory back pressure. For this purpose, high frequency ventilators often incorporate an expiratory compensation valve. HFV circuits also use small-diameter tubing having reduced compressible volume and internal compliance, and are of substantially reduced length to further minimize the column of air in the circuit against which or through which the patient must exhale.

SUMMARY OF THE INVENTION

The present invention is directed to a patient adapter used in a ventilator circuit for connecting gas tubing. The adapter features an expiratory pipe having a diameter which is substantially greater than the diameter of the inspiratory pipe. Internal energy loss of the adapter is minimized by using a relatively small angle of intersection of the inspiratory and expiratory pipes, and also by minimizing the angle at which the patient pipe intersects the junction of the inspiratory and expiratory pipes. The invention includes a new high frequency ventilation circuit incorporating an expiratory tubing limb having a substantially increased diameter as compared to the inspiratory tubing limb. The diameters of the two limbs correspond to the diameters of the patient adapter. More specific features of the invention are set forth in the following detailed description.

DETAILED DESCRIPTION OF THE PREFERRED EMBODIMENTS

Figure 1:
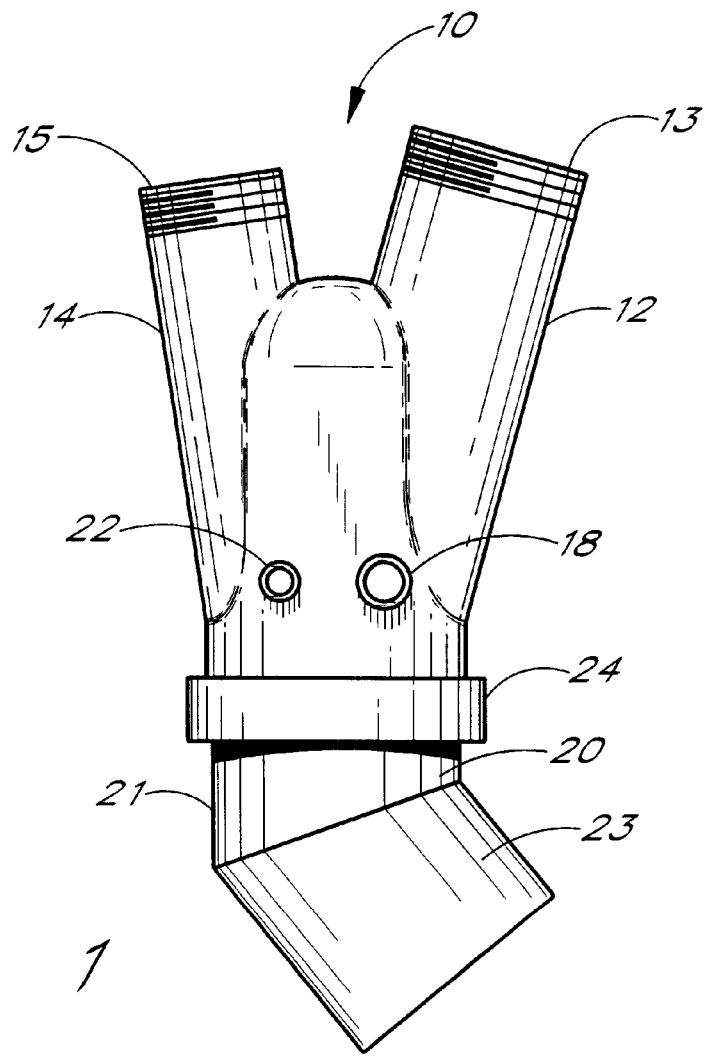
FIG. 1 is top view of the asymmetric patient adapter of the invention.
Figure 2:
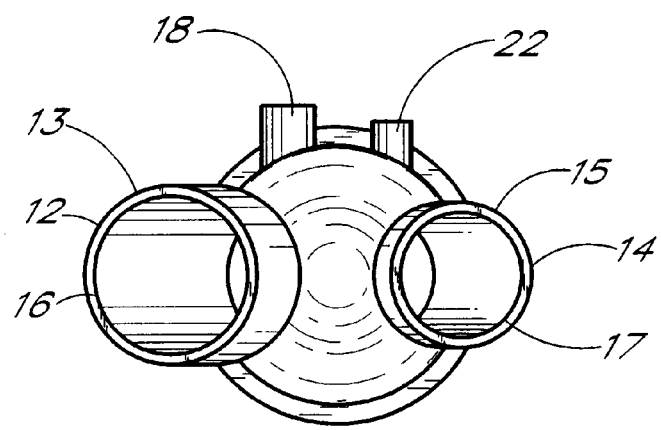
FIG. 2 is an end view of the adapter of the invention.

Referring to FIGS. 1 and 2, there is illustrated the asymmetric patient adapter 10 of the present invention featuring an inspiratory pipe and an expiratory pipe having different diameters. As shown, inspiratory pipe 14 has an interior circular port 17 of a smaller diameter than the diameter of interior circular port 16 of the expiratory pipe 12. Similarly, the outer diameters of the inspiratory and expiratory pipes are different, corresponding substantially to the same difference as the different internal pipe diameters. Typical pipe wall thicknesses are between about 0.5 mm and about 2 mm although such thicknesses are not critical and depend on the design of the pipe.

Both the inspiratory and expiratory pipes extend substantially along respective axes which intersect within the interior of the adapter structure. As shown in FIGS. 1 and 2, each of the pipes are substantially cylindrical along their respective lengths. As particularly seen in FIG. 1, the axes of the pipes extend outwardly from one another at an acute angle, preferably of about 10°, to minimize energy loss and back pressure. It is also preferred to incorporate a patient connector pipe 20 having an angled portion 23 for creating a swivel connection more easily secured to an inlet fitting on an endotracheal or tracheostomy tube. The angle of the angled portion 23 of the patient connector pipe 20 from the axis of the straight portion 21 extending from collar 24 is selected to minimize energy loss and back pressure of gas, during the ventilation cycle. An obtuse angle between the axis of straight portion 21 and angled portion 23 is preferably 60° or less. Patient connector pipe 20 is rotatably secured within collar 24 by a snap fitting or the like, although other equivalent means for forming the rotatable connection between the patient connector pipe and the body of the adapter may be used as understood by those skilled in the art.

Temperature and pressure monitoring ports are preferably formed on the adapter for receiving and connecting pressure and temperature sensing components or devices. For this purpose, a pressure monitor port 22 extends from the body of the adapter as does a temperature monitor port 18. However, the device may incorporate only one or neither of these ports, depending on the desired use, and the requirement for monitoring the temperature and/or pressure of the gas passing through the adapter. The position and configuration of these ports, including rotatable elbow connections and the like may be selected by those skilled in the art.

The difference between the internal diameter of the expiratory pipe and the inspiratory pipe are such that the expiratory pipe inner diameter (ID) is at least about 20% greater than the ID of the inspiratory pipe. More preferably, the expiratory pipe ID is at least about 30%, and most preferably is about 33% (30%–40%) and up to 2 times greater than the ID of the inspiratory pipe. For a preferred adapter used in HFV, the inner diameter of the inspiratory pipe is between about 8 mm and about 12 mm and the diameter of the expiratory pipe is between about 12 mm and about 18 mm. With these preferred parameters, the ratio of the inner diameter of the inspiratory pipe to that of the expiratory pipe is between 1:1.20 and about 1:2 and more preferably between 1:1.3 and 1:1.5, respectively. The outer diameters will depend on the specific internal pipe diameter plus the thickness of the pipe wall. Again, wall thicknesses of between about 0.5 and about 2 mm are used, with about 1 mm being typical. The ends of the outer surface of the pipe may also feature annular ribs for making more secure connections to the tubing secured to the pipe ends.

Figure 3:
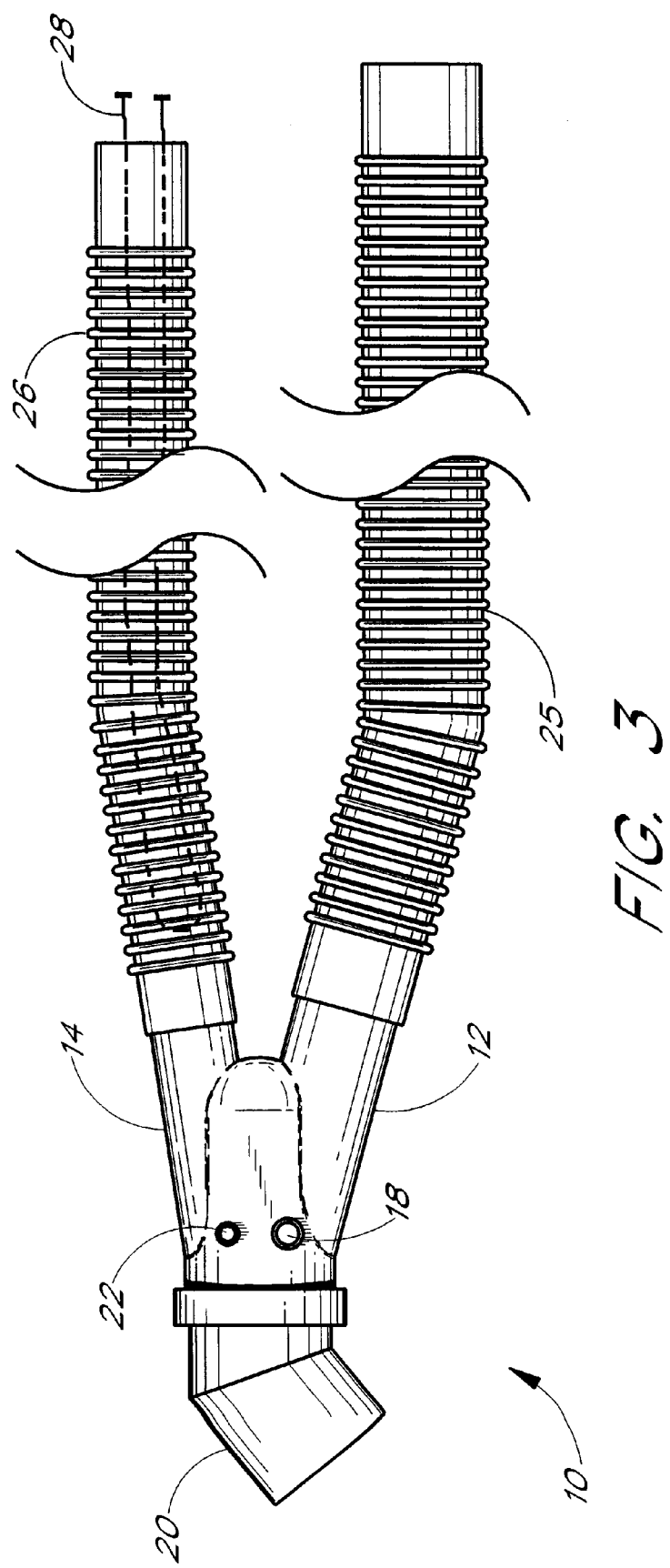
FIG. 3 is a top view of a high frequency ventilator circuit of the invention including the asymmetric patient adapter.

FIG. 3 illustrates a high frequency respiratory circuit incorporating the adapter 10 illustrated in FIGS. 1 and 2. An expiratory limb 25 consists of a length of tubing having one end secured to the end of expiratory pipe 12 of adapter 10, and an inspiratory limb 26 comprising a length tubing secured to the end of inspiratory pipe 14. Any suitable length of tubing may be used. Typically, neonatal circuits are 48 inches long and may incorporate heating wires for heating the gas along the length of the tubing. As illustrated, a heated wire 28 is installed in inspiratory limb 26 illustrating a single-heated limb's circuit. However, dual-heated limbs circuits may be used. Further, the ventilator circuit may also include one or more water traps, for example, as disclosed in U.S. Pat. No. 4,457,305, the description thereof which is incorporated herein by reference. Of course, the size (diameter) of the hose or tubing used in the circuits will correspond to the diameter of the adapter of the circuit as previously discussed.

Although the circuit described above is primarily focused on HFV circuits used in neonatal and infant ventilator configurations, the invention is not to be so limited. Accordingly, the asymmetric patient adapter of the invention is suitable for adult ventilator circuits used with mechanical ventilators, or in anesthesia circuits. These as well as other uses and features of the invention will be understood by those skilled in the art.

What is claimed is:

1. A patient adapter for connecting inspiratory and expiratory gas tubing comprising
    an inspiratory pipe having a first internal diameter,
    an expiratory pipe having a second internal diameter,
    a patient connector pipe communicating with said inspiratory pipe and said expiratory pipe and having a third internal diameter larger than either of said first or said second internal diameter, and
    wherein said second internal diameter is at least about 20% greater than said first internal diameter.

2. A patient adapter of claim 1 wherein said inspiratory pipe extends along a first axis and said expiratory pipe extends along a second axis and wherein said first and second axes form an acute angle.

3. A patient adapter of claim 2 wherein said patient connector pipe extends along a third axis extending from said first and said second axes.

4. A patient adapter of claim 3 wherein said first, second and third axes are substantially coplanar.

5. A patient adapter of claims 1, 2, 3 or 4, wherein said second internal diameter is at least about 30% greater than said first internal diameter.

6. A patient adapter of claims 1, 2, 3 or 4 wherein said patient connector pipe is rotatably secured along a third axis.

7. A patient adapter of claims 1, 2, 3 or 4 including a pressure sensing port.

8. A patient adapter of claims 1, 2, 3 or 4 including a temperature sensing port.

9. A patient adapter of claims 1, 2, 3 or 4 wherein said second internal diameter is about 33% greater than said first internal diameter.

10. A patient adapter of claims 1, 2, 3 or 4 wherein said first internal diameter is between about 8 mm and about 12 mm and said second diameter is between about 12 and about 18 mm and wherein the ratio of said first diameter: second diameter is between about 1:1.3 and about 1:1.5, respectively.

11. A respiratory circuit comprising
    an inspiratory tubing limb including first tubing for directing gas from a source of gas to a patient during inspiration,
    an expiratory tubing limb including second tubing for directing gas from a patient during expiration, and
    an adapter comprising a first pipe having a first internal diameter and connected to said first tubing, a second pipe having a second internal diameter at least about 20% larger than said first diameter and connected to said second tubing, and a third pipe having a third internal diameter greater than either said first or said second internal diameter.

12. A respiratory circuit of claim 11 including one or more heating wires extending along at least a portion of said first tubing and/or said second tubing.

13. A respiratory circuit of claims 11 or 12 wherein said second internal diameter is 30% to 100% larger than said first internal diameter.

14. A respiratory circuit of claim 11 wherein said first internal diameter is between about 8 mm and about 12 mm and said second diameter is between about 12 and about 18 mm and wherein the ratio of said first diameter: second diameter is between about 1:1.3 and about 1:2, respectively.

15. A respiratory circuit of claim 14 wherein said first tubing has an internal diameter of between about 10 mm and about 15 mm, said second tubing has an internal diameter of between about 12 mm and about 20 mm, and wherein the ratio of the internal diameter of said first tubing:internal diameter of said second tubing is between about 1:1.3 and about 1:1.5, respectively.

16. A method of administering high-frequency ventilation comprising utilizing a respiratory circuit of claim 11, 12, 14 or 15, and directing inspiratory gas through said first tubing and directing expiratory gas through said second tubing.

* * * * *